US005686556A

United States Patent [19]

Jouffret et al.

[11] Patent Number: 5,686,556
[45] Date of Patent: Nov. 11, 1997

[54] PROCESS FOR THE PREPARATION OF AN α-AMINO ω-ESTER MONOAMIDE AND PROCESS FOR THE MANUFACTURE OF A POLYAMIDE

[75] Inventors: Frédéric Jouffret, Francheville; Pierre-Jean Madec, Orléans, both of France

[73] Assignee: Rhone-Poulenc Chimie, Courbevoie Cedex, France

[21] Appl. No.: 495,698

[22] PCT Filed: Jan. 21, 1994

[86] PCT No.: PCT/FR94/00073

§ 371 Date: Sep. 14, 1995

§ 102(e) Date: Sep. 14, 1995

[87] PCT Pub. No.: WO94/17030

PCT Pub. Date: Aug. 4, 1994

[30] Foreign Application Priority Data

Jan. 25, 1993 [FR] France ..................... 93 00909

[51] Int. Cl.$^6$ .............. C08G 69/08; C08G 73/10

[52] U.S. Cl. ............ 528/310; 528/335; 528/336; 528/241; 528/272; 525/420

[58] Field of Search ................ 528/272, 336, 528/335, 310, 271; 525/420

[56] References Cited

U.S. PATENT DOCUMENTS 2,214,442 9/1940 Spanagel ................. 528/335
4,722,997 2/1988 Roerdink et al. ......... 528/335

OTHER PUBLICATIONS

Zahn et al, Makromol. Chem 36 (Oct. 1956) pp. 85–119.

*Primary Examiner*—Samuel A. Acquah
*Assistant Examiner*—P. Hampton-Hightower
*Attorney, Agent, or Firm*—Burns, Doane, Swecker & Mathis, L.L.P.

[57] ABSTRACT

Process for producing α-amino ω-ester monoamides such as $H_2N-(CH_2)_6-NH-CO-(CH_2)_4-CO-OCH_3$ by reacting a diacid with a diamide at a diamine/diester molar ratio of 0.8 and 1.2 is provided. Additionally, a novel process for producing a polyamide by homopolymerization of an α-amino ω-ester monoamide is provided.

24 Claims, No Drawings

PROCESS FOR THE PREPARATION OF AN α-AMINO ω-ESTER MONOAMIDE AND PROCESS FOR THE MANUFACTURE OF A POLYAMIDE

FIELD OF THE INVENTION

The invention relates to a process for the preparation of an α-amino ω-ester monoamide, called ester monoamide, and to a process for the preparation of a polymer including amide functional groups.

It relates more particularly to a process for direct preparation of an ester monoamide and to a process for polymerization of this ester monoamide for the production of a polyamide of high viscosity.

BACKGROUND OF THE INVENTION

Polyamides are known synthetic materials discovered at the beginning of the 20th century. Thus, polyhexamethylene adipamide, better known under the name of PA 6,6 or Nylon 6,6 was synthesized for the first time by W. H. Carothers in 1936.

These polyamides are generally employed industrially for the production of synthetic fibres in applications such as textiles or as fibres for reinforcing various materials like elastomers, other plastics, cements and the like.

They are also employed as a matrix resin for the manufacture of moulded articles. In this application they may contain numerous fillers improving especially their mechanical, electrical or fire-resistance properties.

There are two major processes for the manufacture of a polyamide. In the first the polyamide is obtained by homopolymerization of an amino acid such as, for example, caprolactam, which produces a polyamide called PA 6. The polyamides obtained by this first process are generally identified by the letters PA followed by a single number.

In the second process, the polyamide is obtained by reaction between a diamine and a diacid. The best known polyamides manufactured by this second process are PA 6,6, obtained by the action of hexamethylenediamine on adipic acid and PA 6,10, obtained by the action of hexamethylenediamine on sebacic acid. Another class of polyamides obtained by this second process includes aromatic or semi-aromatic polyamides, which exhibit superior mechanical and heat behaviour properties. Polyhexamethylene terephthalate, polyhexamethylene isophthalate or their copolymers may be mentioned as polyamides belonging to this class.

The polymerization process employing this second category of reaction requires control of the stoichiometry between the starting diamine and diacid in order to obtain polymers of high molecular weight. This control is often difficult to carry out because evaporation of one of the reactants generally takes place, making it necessary to add an excess of this reactant to the process and requiring a considerable monitoring of the process control parameters. As a result, obtaining a polymer of very high molecular weight or of high viscosity often makes it necessary to carry out a solid postcondensation, demanding a high consumption of energy and opening up the possibility of giving rise to polymer degradation.

Furthermore, the α-amino ω-ester monoamide derived, for example, from adipic acid and hexamethylenediamine is known, especially from the paper published by Zahn et al. in Makromol. Chem. 36 (1956) 85–119. This product has been identified in the mixture obtained following the reaction between hexamethylenediamine and diethyl adipate and the treatment of the reaction mixture with a solvent. No document describes a process permitting this compound to be synthesized specifically and selectively either directly or by a process of separation and purification.

SUMMARY OF THE INVENTION

The objective of the present invention is especially to overcome these disadvantages by proposing a process for the preparation of an α-amino ω-ester monoamide, enabling this compound to be directly obtained selectively and specifically, and a process for the preparation of polyamides by homopolymerization of the abovementioned α-amino ω-ester monoamide, which is more particularly suited for the preparation of those that are obtained by the second process of manufacture. The process of the invention makes it possible especially to reduce considerably the losses of one of the starting monomers and therefore to have a better control of the stoichiometry.

To this end the invention proposes a process for the preparation of an α-amino ω-ester monoamide of general formula (IV)

$$H_2N-B-NH-CO-A-COOR_1 \qquad (IV)$$

in which
- B denotes a diamine residue and
- A denotes a residue of a diacid
- $R_1$ denotes an alkyl group containing from 1 to 6 carbon atoms, characterized in that it consists:
in mixing a diamine of formula:

$$H_2N-B-NH_2 \qquad (II)$$

and a diester of formula:

$$R_1OOC-A-COOR_1 \qquad (III)$$

in a diamine/diester molar ratio of between 0.8 and 1.2, advantageously between 1 and 1.1,
in keeping this mixture in liquid phase at a temperature below the melting or crystallization temperature of the α-amino ω-ester monoamide formed, until the precipitation of the said α-amino ω-ester monoamide, and in recovering the precipitate formed.

Another subject-matter of the present invention is a process for the preparation of a polymer including repeat units of formula I which follows:

$$-[-CO-A-CO-NH-B-NH-]_n- \qquad (I)$$

in which A and B, which are identical or different, are diacid and diamine residues and denote aliphatic, aromatic, aromatic/aliphatic or aliphatic/aromatic hydrocarbon groups, and
n is a number between 20 and 700.

This process consists in carrying out the homopolymerization of an α-amino ω-ester monoamide of general formula (IV) by heating at least one α-amino ω-ester monoamide to a temperature between 170° C. and 400° C. and in keeping the molten reaction mass, with stirring, at a temperature of between 170° C. and 400° C. until a reaction mass is obtained exhibiting a desired inherent viscosity Iv.

Another subject-matter of the invention consists of a process for the manufacture of a polymer containing repeat units of general formula (I), consisting in carrying out, in a step 1, the preparation of an α-amino ω-ester monoamide, according to the process which forms the first subject-matter of the invention, and in carrying out, in a step 2, the homopolymerization of the α-amino ω-ester monoamide after having isolated and optionally purified, for example by washing, the product manufactured in step 1.

To avoid repetition and for greater clarity, the first two subject-matters of the invention will be described as step 1 and step 2 of the description of the process forming the third subject-matter of the invention.

However, these two steps can be carried out independently. Thus, on the one hand, step 2 can be carried out with an α-amino ω-ester monoamide obtained by a process other than that described in step 1 and, on the other hand, the α-amino ω-ester monoamide obtained in step 1 will be capable of being used in other applications.

In accordance with the invention and especially with the third subject-matter of the latter, the process for the manufacture of a polymer including repeat units of formula (I) includes two successive steps.

In a first step, called step 1, a diamine of formula (II) which follows:

$$H_2N-B-NH_2 \qquad (II)$$

is reacted with a diester of an acid of general formula (III)

$$R_1OOC-A-COOR_1 \qquad (III)$$

in which $R_1$, which are identical or different, denote a hydrocarbon group containing from 1 to 6 carbon atoms, preferably an alkyl group such as, for example, methyl or ethyl radicals.

According to another characteristic of the invention the diamine and the diester of an acid are used in a stoichiometric ratio which is equal to 1 or very near, preferably between 0.8 and 1.2, advantageously between 1 and 1.1.

The precipitate obtained during this step 1 is an α-amino ω-ester monoamide of general formula (IV)

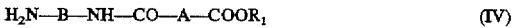

$$H_2N-B-NH-CO-A-COOR_1 \qquad (IV)$$

and its structure has been confirmed by spectral analyses such as $^{13}C$ NMR.

This product can be purified, especially to remove the unreacted starting materials, for example by washing with water.

The product thus obtained is stable in storage at ambient temperature, under inert atmosphere or under air.

Step 1 of the process of the invention makes it possible therefore to obtain an oligomer of a polyamide exhibiting a perfect stoichiometric ratio of the two starting monomers.

Furthermore, during this step 1 the losses of one of the monomers, for example by evaporation, are minimal, because it is performed at a very low temperature, that is to say at a temperature slightly higher than the melting temperature of one of the starting monomers, for example at the melting temperature of the lowest-melting monomer. This temperature will be advantageously 1° to 30° C. higher than the melting temperature.

In a preferred embodiment, step 1 is carried out at a temperature at which at least one of the starting materials is molten, the other being either in molten, solubilized or dispersed form, this temperature being lower than the melting or crystallization temperature of the α-amino ω-ester monoamide. Thus, the latter precipitates as soon as it is formed.

In another embodiment of step 1 of the process of the invention, the starting materials are dissolved in a mutual solvent in which the α-amino ω-ester monoamide is insoluble. Thus, as in the first embodiment, the α-amino ω-ester monoamide will precipitate as soon as it is formed.

According to another characteristic of the invention, step 1 is carried out in the presence of a compound exhibiting a catalytic activity for the aminolysis reaction between the diamine and the diester of an acid. This compound includes electrophilic and/or nucleophilic groups.

Suitable compounds are especially the compounds including a basic group and/or an acidic group.

These compounds can be added to the reaction mixture in quantities by weight of between 0.1% and 10% relative to the diamine/diester mixture.

Suitable compounds for the invention which have a catalytic effect and which may be mentioned are strong acids, strong bases, alkali metal alkoxides such as sodium methoxide, alkali metal aryloxides, aromatic compounds including a phenol functional group, such as phenol, meta- or ortho-cresol, imidazole and organometallic compounds such as, for example, organic titanium or zirconium compounds.

Among the strong acids the preferred compounds of the invention are acids containing phosphorus and their derivatives.

Other compounds including N-heterocyclic groups, such as pyrazole and its derivatives and 8-hydroxyquinoline, can also be employed.

This list is given solely by way of example and is not limitative. In fact, any catalyst of the aminolysis reaction can be suitable for the invention.

However, in a preferred embodiment of the invention, the preferred catalysts of the invention are those that will be capable of being removed before the beginning of the reaction of homopolymerization of the α-amino ω-ester monoamide in step 2, that is to say preferably before the melting temperature of the said α-amino ω-ester monoamide.

This removal of the catalyst can be carried out either during the heating of the α-amino ω-ester monoamide in step 2 of the process, merely by evaporation, or by extraction, for example by washing with water the precipitate obtained in step 1, in advance of step 2.

This removal of the catalytically active compound is not a compulsory condition of the process of the invention. Thus, in the case of some catalysts, At is advantageous to preserve them in the course of step 2, because they can promote the homopolymerization of the compound of formula (IV):

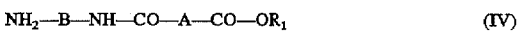

$$NH_2-B-NH-CO-A-CO-OR_1 \qquad (IV)$$

This second step of the process in accordance with the invention consists in carrying out the homopolymerization of the α-amino ω-ester monoamide of formula (Iv) by heating the latter to a temperature of between 170° C. and 400° C. and in keeping the mixture at a temperature of between 170° C. and 400° C. for the time needed to obtain a polymer of high molecular mass. The development of the molecular mass of the polymer is monitored by measuring an inherent viscosity of the reaction mixture (Iv) by a method described below. This temperature range may be different and is variable, depending on the nature of the polymer to be manufactured.

According to a preferred characteristic of the process of the invention the α-amino ω-ester monoamide is melted, the polymerization being carried out in a melt medium. The molten reaction mass is optionally stirred.

According to another characteristic of the invention the holding of the reaction mass at temperature is carried out at a pressure not exceeding atmospheric pressure.

In one embodiment of the invention the heating of the ester monoamide is carried out under reflux up to a temperature of between 170° C. and 400° C. As indicated above, this temperature range may be different and is variable, depending on the nature of the polymer to be manufactured.

During this heating the very volatile products such as the catalysts employed in step 1 and the alcohol formed during the homopolymerization are removed.

After this temperature rise the reaction mass is kept at a temperature which is advantageously higher than 170° C., at atmospheric pressure. The polymerization is advantageously ended by lowering the pressure above the reaction mass to a value which may advantageously lie between $10^2$ and $10^5$ Pa, it being possible for the temperature to be slightly increased.

When the reaction mixture has reached the desired viscosity it is cooled.

In another embodiment the α-amino ω-ester monoamide of formula (IV) is heated directly to a temperature which is advantageously between 170° C. and 400° C., the pressure above the reaction mass being reduced during the heating period for example, not later than when the α-amino ω-ester monoamide is melted. The temperature range given above is merely indicative and my vary depending on the nature of the polymer to be synthesized, as indicated for the first embodiment of step 2.

The reaction mass is kept at this temperature for a sufficient period to obtain a polymer which has the desired molecular and viscosity characteristics. The polymer thus obtained is then cooled.

The process of the invention thus makes it possible to obtain a polyamide whose spectral analyses show it to be wholly comparable with that obtained by polymerization starting with a salt formed by a diacid with a diamine, a salt generally called "Nylon salt" when the polyamide is a polyhexamethylene adipate.

Furthermore, as the examples below will illustrate, the kinetics of polymerization of the α-amino ω-ester monoamide are very fast. Moreover, it is possible to reach high molecular weights and viscosity directly using the polymerization process in melt or solid medium.

Analyses of the polymers obtained show that their degradation and the presence of compounds produced by secondary reactions are very limited and do not exceed those present in the known polymerization processes starting with diacids and diamines.

The process of the invention can be used for the production of many polyamides. In fact, the process is applicable as soon as it is possible to manufacture an α-amino ω-ester monoamide selectively, that is to say that the latter can be obtained by precipitation, as soon as it is formed, from the reaction mixture containing the starting monomers, as in step 1 described above, forming the first subject-matter of the invention, or by another process.

Thus, the process of the invention is applicable for manufacturing polymers including repeat units of formula (I) in which radical A denotes a hydrocarbon group chosen from the group including linear or branched aliphatic radicals containing from 1 to 16 carbon atoms, aromatic radicals containing 1 or a number of aromatic nuclei in condensed or uncondensed form, aromatic radicals containing a number of aromatic nuclei joined to one another by an aliphatic radical containing from 1 to 6 carbon atoms or a valency bond, and the radical B denotes a hydrocarbon group chosen from the group including linear or branched aliphatic radicals containing from 1 to 16 carbon atoms or radicals containing one or a number of aromatic nuclei joined to nitrogen atoms by an aliphatic radical, in condensed or uncondensed form, or joined to one another by a valency bond or an aliphatic radical.

Radical A is advantageously chosen from the group including polymethylene radicals which are unsubstituted or substituted by alkyl groups and benzoic and/or alkyldiphenylene radicals.

Preferred radicals which may be mentioned are: hexamethylene, pentamethylene, tetramethylene, 2-methylpentamethylene, 2-ethylpentamethylene, meta-phenylene and para-phenylene radicals.

Similarly, radical B is chosen from the group including polymethylene radicals which are unsubstituted or substituted by alkyl groups, such as, for example, pentamethylene, tetramethylene, 2-methylpentamethylene and 2-ethylpentamethylene radicals.

Furthermore, the polymer obtained according to the process of the invention may include a number of repeat units of general formula (I) differing from one another in at least one of the radicals A and B. It is possible to mention especially the copolymers including repeat units containing, in the case of some, the para-phenylene radical as radical A and, in the case of others, the meta-phenylene radical as radical A and/or, in the case of some, the hexamethylene radical as radical B and, in the case of others, the alkylpentamethylene radical as radical B.

The polyamides produced by the process of the invention can be employed in many applications such as film, yarns, fibres or moulded compositions, as is well known in the field of the art.

Other details, characteristics and advantages of the invention will appear more clearly in the light of the examples given below solely by way of indication.

The process of the invention includes two distinct steps, namely:

a step 1 which consists in manufacturing an ester monoamide of general formula (IV) by reaction of a diamine with a diester. Examples 1 to 11 will illustrate this step 1 and the first subject-matter of the invention, a step 2 of homopolymerization of the monoamide described below. This step and the second subject-matter of the invention are illustrated by Examples 12 to 20.

EXAMPLES 1 TO 6

Preparation of the Compound

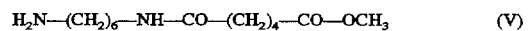  (V)

1.03 mmol of hexamethylenediamine is melted in a reactor. 1 mol of dimethyl adipate is added and the mixture is stirred under a nonoxidizing atmosphere such as nitrogen. The catalyst is then added.

The mixture is kept at a temperature of 50° C. After a few minutes a precipitate appears. At the end of a few hours (2 to 10 hours) the reaction mixture has set solid.

The product obtained is washed with water to remove especially the starting materials. The product is then dried under vacuum and when cold.

The product obtained is characterized by steric exclusion chromatography (SEC) and $^{13}C$ NMR analysis of the solid.

These analyses confirm the formation of an amide functional group and the preservation of an ester functional group. They show that the product obtained is specifically the product of formula

$$H_2N-(-CH_2)_6-NH-CO-(CH_2)_4-CO-O-CH_3 \quad (V)$$

This product is obtained in a weight yield of the order of 90%.

The results of several examples carried out with different catalysts are grouped in Table I below.

TABLE I

| Ex. | Catalyst | Catalyst weight % | Temperature | Time |
| --- | --- | --- | --- | --- |
| 1 | NaOCH$_3$ | 1 | 50° C. | 5 h |
| 2 | NaOCH$_3$ | 5 | 50° C. | 5 h |
| 3 | NaOCH$_3$ | 10 | 50° C. | 10 min |
| 4 | phenol | 5 | 50° C. | 5 h |
| 5 | resorcinol | 10 | 50° C. | 5 h |
| 6 | benzoic acid | 5 | 50° C. | 5 h |

EXAMPLES 7 TO 9

Synthesis of Other Aliphatic Ester Monoamides of Formula:

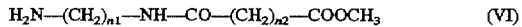

$$H_2N-(CH_2)_{n1}-NH-CO-(CH_2)_{n2}-COOCH_3 \quad (VI)$$

This synthesis is carried out according to the procedure described for Examples 1 to 6, also at a temperature of 50° C.

The products were obtained in a yield of the order of 90%. The structure and the purity of these products have been confirmed by conventional spectral analyses described above.

The different monoamides synthesized are described in Table II below.

TABLE II

| | Starting materials | | | | Monoamide |
| --- | --- | --- | --- | --- | --- |
| Ex. | H$_2$N—(CH$_2$)$_{n1}$—NH$_2$ | CH$_3$—OOC—(CH$_2$)$_{n2}$—COOCH$_3$ | Catalyst % | Synthesis T°C. | Formula |
| 7 | n1 = 12 | n2 = 4 | 5% phenol | 70 | n1 = 12<br>n2 = 4 |
| 8 | n1 = 6 | n2 = 6 | 5% phenol | 50 | n1 = 6<br>n2 = 6 |
| 9 | n1 = 6 | n2 = 8 | 5% phenol | 50 | n1 = 6<br>n2 = 8 |

EXAMPLE 10

Synthesis of the α-amino ω-ester Monoamide of Formula:

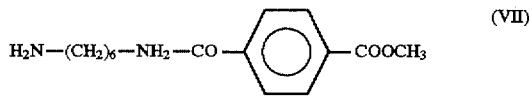

(VII)

One mole of dimethyl terephthalate and 1.03 mol of hexamethylenediamine are introduced. The mixture kept under nitrogen atmosphere is melted. It is then kept, with stirring, at a temperature slightly above the melting temperature, that is to say 160° C.

After 30 minutes and in the absence of catalyst the formation of a precipitate is observed. The reaction is continued until the reaction mixture sets solid. After cooling and grinding, the product is washed with water.

Spectral analyses show that the product has the structure of the formula (VII).

EXAMPLE 11

Synthesis of the Monoamide of Formula:

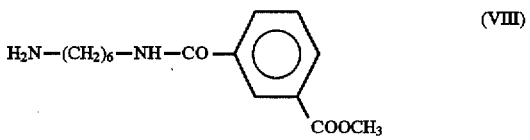

(VIII)

This ester monoamide is obtained by using the procedure of Example 10 with replacement of dimethyl terephthalate with dimethyl isophthalate. The reaction temperature is 90° C.

The following examples illustrate the embodiments of the process for polymerization of the α-amino ω-ester monoamides synthesized in Examples 1 to 11, and therefore step 2 of the process, and the second subject-matter of the invention.

EXAMPLE 12

In a first embodiment of a process for polymerization (called method A) of an α-amino ω-ester monoamide, the latter, after having been optionally ground, is introduced into a reactor fitted with a condenser.

The α-amino ω-ester monoamide is heated at reflux for one hour at a temperature varying from 200° to 270° C.; during this period a vigorous release of methanol, due to the oligomerization reaction, is observed.

After the reflux has stopped, the reaction mixture is kept at 270° C. for 5 hours with stirring.

To obtain a higher degree of polymerization the reaction mixture is kept at reduced pressure for a period of 2 hours, still at the temperature of 270° C.

In a second embodiment of a process for polymerization (called method B) of the α-amino ω-ester monoamide, the latter is kept at reduced pressure and with stirring as soon as it is heated to a temperature of the order of 270° C. This application of reduced pressure is advantageously carried out after the melting of the α-amino ω-ester monoamide.

In the examples summarized below in Table III the polymerization was stopped when the reaction mass was wrapping itself around the stirrer.

The polyamides obtained were characterized by measuring an inherent viscosity (Iv) enabling the molecular mass $\overline{M}n$ to be assessed.

Furthermore, the structure of the polyamide and its purity, that is to say the presence of a nonlinear structure due to secondary reactions, were determined by $^{13}$C NMR spectral analyses of the solid, $^{13}$C NMR of the liquid and by eretic exclusion chromatography.

These various analyses show that the polymerization of an α-amino ω-ester monoamide produces a polymer exhibiting structural characteristics which are identical with or quite similar to those of a conventional polyamide obtained by polymerization of the "Nylon salt", that is to say of the salt formed by the diamine with the diacid.

Furthermore, the process of the invention makes it possible to obtain high degrees of polymerization very rapidly, because in the case of a PA 66 an inherent viscosity higher than 1.5 is obtained after 2 hours' holding at 270° C. at reduced pressure, this value not appearing to be a limit.

The characteristics of the polymers obtained according to the two embodiments of the process for polymerization of the invention are summarized in Table III below, in comparison with a polyamide obtained by the conventional process.

These characteristics are:

Iv: Inherent viscosity measured on the polymer. This viscosity is determined at 30° C. on a solution containing 0.5 g of polymer in 100 cm$^3$ of meta-cresol Tm: Melting temperature of the polymer, determined by DSC (differential scanning calorimetry) analysis $\overline{\text{Mn}}$: number molecular mass, determined by stearic exclusion chromatography $\overline{\text{Mw}}$: absolute weight molecular mass estimated from a polystyrene calibration.

Furthermore, thermogravimetric investigation shows that the polymers obtained according to the process of the invention are as stable thermally as the polymers obtained by the conventional processes.

The above examples clearly show that the process of the invention makes it possible to obtain polymers that are structurally similar to the polymers obtained by the conventional processes. However, the process of the invention makes it possible to obtain polymers of higher degree of polymerization or molecular mass, with faster polymerization kinetics.

Moreover, it is not necessary to introduce a large excess of one of the reactants, for example the diamine, because the evaporation losses are reduced to a minimum, the diamine being present only in step 1, which is carried out at a relatively low temperature.

We claim:

1. A process for the preparation of an α-amino ω-ester monoamide of formula (IV):

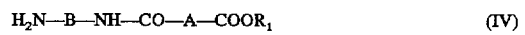

in which:

B denotes a diamine residue and

A denotes a residue of a diacid $R_1$ denotes an alkyl group containing from 1 to 6 carbon atoms, said process comprising mixing a diamine of formula:

TABLE III

| Ex. | Ester monoamide | Polymerization process | Polymerization time | IV | Tm | $\overline{\text{Mn}}$ | Absolute $\overline{\text{Mw}}$ |
|---|---|---|---|---|---|---|---|
| 12 | ex. 1 | method A | 8 h | 0.33 | 228.2 | 4670 | 4590 |
| 13 | ex. 4 | method B | 3 h | 1.55 | 256 | 18100 | 50200 |
| 14 | ex. 5 | method A | 8 h | 1.18 | 251.7 | 13600[1] | 24570 |
| 15 | ex. 5 | method B | 3 h | 1.44 | 252.2 | 17700 | 54420 |
| 16 | ex. 6 | method B | 3 h | 0.89 | 256.6 | 14700 | 24570 |
| 17 | ex. 7 | method B | 3 h | 1.16 | 226.1 | 20400 | 32000 |
| 18 | ex. 8 | method B | 3 h | 0.60 | 225.3 | 9973 | 11500 |
| 19 | ex. 9 | method B | 3 h | 0.80 | 217.6 | 12200 | 17950 |
| 20 | ex. 10 | method B | 2 h | 0.90 | 370[2] | 11000 | 92430 |

(1) $\overline{\text{Mn}}$ calculated from the measurement of an inherent viscosity
(2) Melting of the polymer accompanied by its degradation.

By way of comparison, the characteristics of a polyamide 6,6 obtained by the polymerization of a salt of diamine and diacid (Nylon salt) and of polymers obtained by polymerization of a diamine/diester mixture are collated in Table IV below.

TABLE IV

| Ex. | Polymer | IV | Tm | $\overline{\text{Mn}}$ | Absolute $\overline{\text{Mw}}$ |
|---|---|---|---|---|---|
| A | PA 6,6 ex "Nylon salt" | 1.40 | 259.4 | 17100 | 33000 |
| B | PA 12,6 ex "diamine/diester" | 0.49 | 220.8 | 8730 | 13250 |
| C | Polyhexamethylene terephthalate ex "diamine/diester" | 0.43 | 368[1] | 5312 | 31800 |

(1) Melting of the polymer accompanied by degradation and a diester of formula:

in a molar ratio of between 0.8 and 1.2, maintaining the mixture in liquid phase at a temperature below the melting or crystallization temperature of the α-amino ω-ester monoamide formed, until the precipitation of the said α-amino ω-ester monoamide, and recovering the precipitate formed.

2. A process according to claim 1, wherein the molar ratio of the diamine to the diester is between 1 and 1.1.

3. A process according to claim 1, wherein the reaction is continued until the mixture sets solid.

4. A process according to claim 1, wherein the diamine/diester mixture is melted, and the reaction temperature being from 1° to 30° C. higher than the melting temperature of the mixture.

5. A process according to claim 1, wherein the diamine and the diester are dissolved in a solvent, the latter not being a solvent for the α-amino ω-ester monoamide.

6. A process according to claim 1, wherein the reaction is carried out in the presence of a compound which is catalytically active in the aminolysis reaction.

7. A process according to claim 6, wherein the catalytically active compound is present in a weight ratio of between 0.1 and 10% relative to the mass of the mixture.

8. A process according to claim 6, wherein the catalytically active compound is a compound including a nucleophilic group and/or an electrophilic group.

9. A process according to claim 8, wherein the catalytically active compound is a compound having a basic group selected from the group consisting of strong bases, alkali metal alkoxides, alkali metal aryloxides and/or an acid group chosen from the group including strong acids, acids and derivatives containing phosphorus, organometallic compounds, phenols, cresols and derivatives.

10. A process according to claim 8, wherein the catalytically active compound is a compound having an N-heterocyclic group selected from the group consisting of pyrazole and its derivatives and 8-hydroxyquinoline.

11. A process according to claim 1, wherein the radical A denotes an aliphatic, aromatic, aromatic/aliphatic or aliphatic/aromatic hydrocarbon group.

12. A process according to claim 11, wherein the radical A is selected from the group consisting of linear or branched aliphatic radicals containing from 1 to 16 carbon atoms, aromatic radicals including one or a number of aromatic nuclei in condensed or uncondensed form or joined to one another by a valency bond or an aliphatic radical containing from 1 to 6 carbon atoms.

13. A process according to claim 12, wherein the radical A is selected from the group consisting of linear or substituted polymethylene radicals and para- or meta-phenylene radicals.

14. A process according to claim 1, wherein the radical B denotes a hydrocarbon group selected from the group consisting of linear or branched aliphatic radicals containing from 1 to 16 carbon atoms, and radicals including one or a number of aromatic nuclei joined to nitrogen atoms by an aliphatic radical, in condensed or uncondensed form, or joined to one another by a valency bond or an aliphatic radical.

15. A process according to claim 14, wherein the radical B denotes a hexamethylene, pentamethylene, tetramethylene, 2-methylpentamethylene or 2-ethylpentamethylene radical.

16. A process for the preparation of a polymer including repeat units of formula (I):

—[—CO—A—CO—NH—B—NH—]$_n$     (I)

in which:

A denotes a diacid residue

B denotes a diamine residue n is a number between 20 and 700

, said process comprising heating at least one α-amino ω-ester monoamide, of formula (IV)

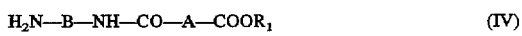

$H_2N$—B—NH—CO—A—$COOR_1$     (IV)

to a temperature of between 170° C. and 400° C., maintaining the reaction mass at a temperature of between 170° C. and 400° C. until a desired inherent viscosity is obtained.

17. A process according to claim 16, wherein the reaction mass is melted.

18. A process according to claim 16, wherein the reaction mass is maintained at a temperature of between 170° C. and 400° C. at a pressure not exceeding atmospheric pressure.

19. A process according to claim 16, wherein the heating of the α-amino ω-ester monoamide is carried out at least partially with a reflux, the holding at temperature being carried out without reflux.

20. A process according to claim 16, wherein the holding at temperature is carried out at least in its terminal stage at reduced pressure.

21. A process according to claim 16, wherein at least the period of heating of the α-amino ω-ester monoamide and the holding at temperature are performed at reduced pressure.

22. A process according to claim 16, wherein said process includes as a first step the manufacture of the α-amino ω-ester monoamide(s).

23. A process according to claim 22, wherein the α-amino ω-ester monoamide(s) is/are washed with water before being introduced into the polymerization step.

24. A process according to claim 22, wherein the catalytically active compounds present in step 1 are removed before the step of heating of the α-amino ω-ester monoamide or during this step of heating.

* * * * *